United States Patent
Duan et al.

(10) Patent No.: US 11,826,015 B2
(45) Date of Patent: Nov. 28, 2023

(54) SYSTEM AND METHOD FOR CONTROLLING CAPSULE ENDOSCOPE

(71) Applicant: Ankon Medical Technologies (Shanghai) Co., LTD, Shanghai (CN)

(72) Inventors: Xiaodong Duan, Pleasanton, CA (US); Qingqing Wang, Shanghai (CN)

(73) Assignees: ANKON MEDICAL TECHNOLOGIES (SHANGHAI) CO., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 0 days.

(21) Appl. No.: 17/917,241

(22) PCT Filed: Apr. 8, 2021

(86) PCT No.: PCT/CN2021/085891
§ 371 (c)(1),
(2) Date: Mar. 13, 2023

(87) PCT Pub. No.: WO2021/204182
PCT Pub. Date: Oct. 14, 2021

(65) Prior Publication Data
US 2023/0225583 A1    Jul. 20, 2023

(30) Foreign Application Priority Data
Apr. 8, 2020    (CN) .......................... 202010268293.7

(51) Int. Cl.
*A61B 1/00*    (2006.01)
*A61B 1/04*    (2006.01)
(Continued)

(52) U.S. Cl.
CPC ...... *A61B 1/00006* (2013.01); *A61B 1/00097* (2022.02); *A61B 1/00158* (2013.01);
(Continued)

(58) Field of Classification Search
CPC .......................... A61B 1/00097; H04N 23/698
See application file for complete search history.

(56) References Cited

U.S. PATENT DOCUMENTS 5,836,894 A * 11/1998 Sarvazyan ............... A61B 8/12
                                                    600/587
6,418,082 B1 * 7/2002 Hollis ................... G01S 3/8036
                                                    367/118
(Continued)

FOREIGN PATENT DOCUMENTS

CN    1636230 A    7/2005
CN    102176855 A    9/2011
(Continued)

*Primary Examiner* — John P Leubecker
*Assistant Examiner* — Jae Woo
(74) *Attorney, Agent, or Firm* — Treasure IP Group, LLC

(57) ABSTRACT

A system and method for controlling a capsule endoscope is provided. The control method includes: measuring a magnetic field value of the environment in which the capsule endoscope is subjected; obtaining a critical magnetic field value for suspension of the capsule endoscope according to the magnetic field value; adjusting a traction force on the capsule endoscope according to the critical magnetic field value for suspension; and controlling the movement of the capsule endoscope in a horizontal and/or vertical direction, wherein the movement of the first magnet is controlled by moving the second magnet, and the capsule endoscope is in a quasi-suspended state as moving in the horizontal and/or vertical direction. The system and method reduce friction between the capsule endoscope and wall of the target area during movement by controlling the capsule endoscope in a quasi-suspended state, which makes the scanning of the target area more accurate.

19 Claims, 7 Drawing Sheets

(51) Int. Cl.
  *H04N 23/698* (2023.01)
  *A61B 1/273* (2006.01)
  *A61B 5/06* (2006.01)
  *A61B 90/00* (2016.01)

(52) U.S. Cl.
  CPC ............ *A61B 1/041* (2013.01); *A61B 1/2736* (2013.01); *A61B 5/061* (2013.01); *H04N 23/698* (2023.01); *A61B 2090/067* (2016.02)

(56) References Cited

U.S. PATENT DOCUMENTS

| | | | | |
|---|---|---|---|---|
| 6,486,877 | B1* | 11/2002 | Watanabe | G06T 17/10 345/420 |
| 8,790,247 | B2* | 7/2014 | Kawano | A61B 1/045 600/117 |
| 2004/0249247 | A1* | 12/2004 | Iddan | A61B 1/00183 600/170 |
| 2004/0264754 | A1* | 12/2004 | Kleen | A61B 1/00158 382/128 |
| 2006/0152309 | A1* | 7/2006 | Mintchev | H02N 15/00 335/58 |
| 2007/0185381 | A1* | 8/2007 | Kimoto | A61B 1/00181 600/117 |
| 2008/0221592 | A1* | 9/2008 | Kawai | A61B 1/00078 606/130 |
| 2008/0306340 | A1* | 12/2008 | Uchiyama | A61B 1/00158 600/117 |
| 2009/0005639 | A1* | 1/2009 | Kawano | A61B 1/041 600/109 |
| 2009/0097725 | A1* | 4/2009 | Krupnik | A61B 1/041 382/128 |
| 2010/0242595 | A1* | 9/2010 | Paine | G01F 23/0038 73/304 C |
| 2010/0268026 | A1* | 10/2010 | Takizawa | A61B 1/00158 600/117 |
| 2011/0179988 | A1* | 7/2011 | Howard | H10N 10/00 114/337 |
| 2011/0253558 | A1* | 10/2011 | Lewis | F17C 1/007 137/1 |
| 2011/0292196 | A1* | 12/2011 | Kawano | A61B 5/062 348/E7.091 |
| 2012/0095290 | A1* | 4/2012 | Kawano | A61B 1/00158 600/117 |
| 2012/0265015 | A1* | 10/2012 | Kawano | A61B 1/00156 600/118 |
| 2013/0030261 | A1 | 1/2013 | Mintchev | |
| 2013/0261410 | A1* | 10/2013 | Davenport | A61B 5/1114 600/302 |
| 2014/0288416 | A1* | 9/2014 | Mahoney | A61B 1/00158 600/118 |
| 2020/0187764 | A1* | 6/2020 | Zeien | A61B 1/041 |

FOREIGN PATENT DOCUMENTS

| | | |
|---|---|---|
| CN | 102573601 A | 7/2012 |
| CN | 103222842 A | 7/2013 |
| CN | 105559739 A | 5/2016 |
| CN | 105962879 A | 9/2016 |
| CN | 107773205 A | 3/2018 |
| CN | 109620104 A | 4/2019 |
| CN | 110575118 A | 12/2019 |
| CN | 110809426 A | 2/2020 |

* cited by examiner

SYSTEM AND METHOD FOR CONTROLLING CAPSULE ENDOSCOPE

CROSS-REFERENCE OF RELATED APPLICATIONS

The application is a National Phase Application of PCT International Application No. PCT/CN2021/085891, International Filing Date Apr. 8, 2021, published Oct. 14, 2021, as International Publication Number WO2021/204182A1, which claims priority from Chinese Patent Application No. 202010268293.7, filed Apr. 8, 2020, all of which are incorporated herein by reference in their entirety.

FIELD OF INVENTION

The present invention relates to the art of a capsule endoscope, and more particularly to a system and method for controlling the capsule endoscope.

BACKGROUND

With the development of magnetically controlled capsule endoscopy, the accuracy of a magnetically controlled capsule endoscope during gastric examination has been consistent with that of conventional gastroscopy, which is a comfortable and safe way to perform gastric endoscopy. The magnetically controlled capsule endoscope includes a magnet inside, and the movement of the capsule endoscope in the stomach is controlled by the force of interaction between an external magnet and an internal magnet thereby.

When using the magnetically controlled capsule endoscope, a dragging walk over the surface of the stomach is generally used. Although this approach is an intuitive way of control, it usually has uncertainty leading to failure of the dragging walk because of the friction between the capsule endoscope and the stomach wall related to the local environment and the forces on the capsule endoscope.

SUMMARY OF THE INVENTION

The present invention discloses a system and a method for controlling a capsule endoscope. Specifically, the traction force required to make the capsule endoscope in a quasi-suspended state is calculated by detecting the location of the capsule endoscope so that the friction between the capsule endoscope and the wall of a target area is greatly reduced and therefore it is easier to move the capsule.

According to an aspect of the present invention, there is provided a system for controlling a capsule endoscope comprising: a capsule endoscope, the capsule endoscope comprising an image acquisition module, a first magnet, a battery module, a wireless module and a sensor module; a control unit for receiving data transmitted from the capsule endoscope to calculate a critical magnetic field value for suspension and obtaining a control signal based on the critical magnetic field value for suspension; a movement unit and a second magnet, the movement unit controlling the second magnet to move in a horizontal and/or vertical direction according to the control signal, wherein the movement of the first magnet is controlled by moving the second magnet, and the capsule endoscope is in a quasi-suspended state as moving in the horizontal and/or vertical direction.

Preferably, the sensor module comprises a magnetic sensor and an acceleration sensor.

Preferably, the magnetic sensor is located away from the first magnet and the acceleration sensor is a gravity sensor.

Preferably, the sensing directions of the magnetic sensor and the acceleration sensor are along the long axis of the capsule endoscope.

Preferably, the direction of magnetization of the first magnet is along the long axis of the capsule endoscope.

Preferably, there is an angle between the direction of magnetization of the second magnet and the vertical direction, and the angle has a magnitude of 0-20°.

Preferably, the movement unit comprises a robot with three-dimensional movement, a right angle coordinate robot or a robotic arm.

Preferably, the second magnet comprises a permanent magnet or an electromagnet.

Preferably, the control system further comprises: an image unit, which is used for receiving a plurality of images captured by the capsule endoscope and building a three-dimensional spatial structure for the target area.

Preferably, the image unit obtains a panoramic image of the target area according to the captured images, and the image unit obtains the three-dimensional spatial structure of the target area according to the panoramic image.

Preferably, the control system further comprises: a locating unit, which is used for recording position information and/or movement trajectory of the capsule endoscope. The image unit obtains the three-dimensional spatial structure of the target area according to the position information and/or movement trajectory.

Preferably, the means for controlling the movement of the second magnet in the horizontal and/or vertical direction comprises manual control means controlled by the movement unit and automatic control means controlled by the control unit.

According to another aspect of the present invention, there is provided a method for controlling the capsule endoscope. The capsule endoscope comprises a first magnet inside the capsule endoscope, and a second magnet outside the capsule endoscope controls the movement of the capsule endoscope. The method comprises: measuring a magnetic field value of an environment in which the capsule endoscope is subjected; obtaining a critical magnetic field value for suspension of the capsule endoscope according to the magnetic field value; adjusting a traction force on the capsule endoscope according to the critical magnetic field value for suspension; and controlling the movement of the capsule endoscope in the horizontal and/or vertical direction, wherein the movement of the first magnet is controlled by moving the second magnet, and the capsule endoscope is in a quasi-suspended state as moving in the horizontal and/or vertical direction.

Preferably, the magnetic field value is measured by a magnetic sensor.

Preferably, the critical magnetic field value for suspension is obtained based on the gravitational force of the capsule endoscope, tilt angle of the capsule endoscope and buoyancy force of the capsule endoscope.

Preferably, the step of adjusting the traction force on the capsule endoscope according to the critical magnetic field value for suspension comprises: obtaining a corrected magnetic field value according to the critical magnetic field value for suspension; adjusting the height of the second magnet according to the corrected magnetic field value, thereby adjusting the traction force on the capsule endoscope.

Preferably, when the tilt angle of the capsule endoscope is greater than zero, it is determined that the capsule endoscope encounters an obstacle.

Preferably, when the capsule endoscope encounters an obstacle, the capsule endoscope is controlled to move in the vertical direction by a change in magnetic field gradient of the second magnet in the vertical direction, and the capsule endoscope is controlled to move in the horizontal direction by manipulating the second magnet to move in the horizontal direction to cross the obstacle.

Preferably, the means for controlling the movement of the capsule endoscope in the horizontal and/or vertical direction comprises manual control means and automatic control means.

According to the aspects of the present invention, the capsule endoscope is controlled to be in a quasi-suspended state, that is, the mutual attraction between the second magnet and the first magnet is equal to or slightly greater than the weight of the capsule endoscope when it is at the upper wall of the target area, equal to or slightly less than the weight of the capsule endoscope when it is at the lower wall of the target area, and offsets the buoyancy force when there is liquid in the target area, so that the pressure between the capsule endoscope and the wall of the target area tends to zero, friction is greatly reduced, and the scanning of the target area is more accurate.

According to the aspects of the present invention, when the capsule endoscope encounters an obstacle, the capsule endoscope is controlled to move in the vertical direction by a change in magnetic field gradient of the second magnet in the vertical direction, so as to achieve the purpose of crossing the obstacle.

According to the aspects of the present invention, two control methods, i.e., automatic scanning and manual scanning are provided. If the position of interest is visible from the image captured by the automatic scanning method, the capsule endoscope can be controlled by the manual scanning method to move to the designated position of the target area for scanning, which improves the efficiency and accuracy of examination.

BRIEF DESCRIPTION OF THE DRAWINGS

The above and other objects and advantages of the present invention will be apparent upon consideration of the following detailed description, taken in conjunction with the accompanying drawings, in which the reference characters refer to like parts throughout and in which.

DETAILED DESCRIPTION

Figure 1:
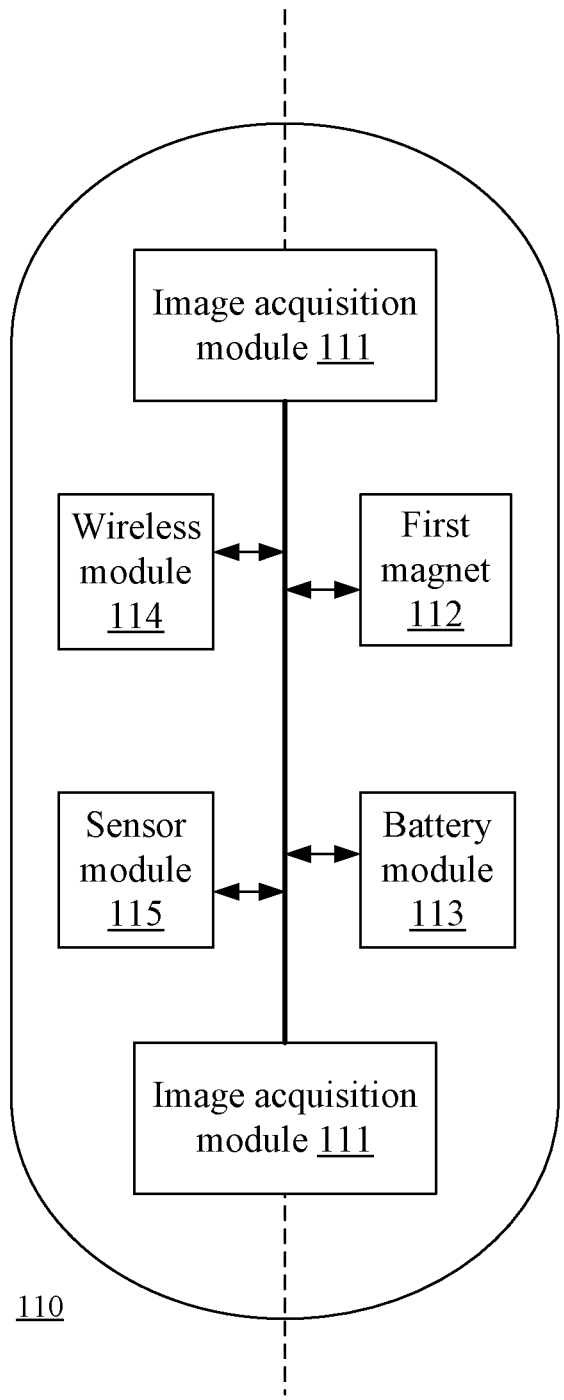
FIG. 1 is a schematic illustration of a capsule endoscope according to an embodiment of the present invention.

The present invention will be understood and appreciated more fully from the following detailed description taken in conjunction with the appended figures. Various exemplary embodiments are well illustrated in the accompanying figures with the intent that these examples not be restrictive. In the drawings, the same elements are represented by the same or similar markings. For simplicity and clarity of illustration, elements shown in the drawings have not been drawn to scale.

In a method of controlling the movement of a capsule endoscope, the movement of the capsule endoscope in the target area (e.g., stomach) is generally controlled by controlling the interaction force between a magnet outside the capsule endoscope and a magnet inside the capsule endoscope. The target area is a confined space, which may be, for example, a bionic stomach, a stomach model, an isolated animal stomach, or a human stomach. Such movement is dragging on the surface of the target area. Although this means of movement is intuitive, it usually has uncertainty leading to failure of the dragging since the friction between the capsule endoscope and the wall of the target area (e.g., stomach wall) is related to local environment and the forces on the capsule endoscope.

Specific embodiments of the present invention are described in further detail below in conjunction with the accompanying drawings.

According to the aspects of the present invention, the interaction force between a second magnet outside the capsule endoscope and a first magnet inside the capsule endoscope is controlled to make the capsule endoscope in the target area in a quasi-suspended state, thus greatly reducing the friction between the capsule endoscope and the wall of the target area (e.g., stomach wall), and improving the efficiency of movement.

The quasi-suspended state is a state in which a downward force received by the capsule endoscope is approximately equal to an upward force received by the capsule endoscope, and the capsule endoscope is roughly suspended without vertical movement in a vertical direction in the air without support. In this state, the friction on the wall of the target area (e.g., the stomach wall) is greatly reduced when the capsule endoscope is moved horizontally.

FIG. 1 is a schematic illustration of a capsule endoscope according to an embodiment of the present invention. As shown in FIG. 1, the capsule endoscope 110 comprises at least an image acquisition module 111, a first magnet 112, a battery module 113, a wireless module 114, and a sensor module 115.

Wherein, there may be one or two image acquisition modules 111, which are used to capture images of the target area and output image data.

The first magnet 112 drives the capsule endoscope 110 to move by the force of interaction with an external magnet outside the capsule endoscope 110. The polarization direction of the first magnet 112 is along the long axis of the capsule endoscope 110 (shown as a dashed line in FIG. 1).

The wireless module 114 transmits image data and sensed data to an external device through wireless communication.

The sensor module 115 comprises an acceleration sensor and a magnetic sensor, the acceleration sensor for measuring tilt angle of the capsule endoscope and the magnetic sensor for measuring a magnetic field value of an environment in which the capsule endoscope is subjected (hereinafter referred to as "ambient magnetic field"). The sensor module 115 further comprises a sensor for detecting the presence of liquid in the target area and for measuring buoyancy force of the liquid. In other embodiments, the acceleration sensor may be a gyroscope or a gravity sensor to measure the tilt angle of the capsule endoscope.

The magnetic sensor should be located away from the first magnet to avoid saturation. The reading of the magnetic field of the capsule endoscope 110 when it is away from the magnetic field source (e.g., an external magnet outside the capsule endoscope) is taken as the reading of the first magnet 112. The ambient magnetic field of the capsule endoscope measured by the magnetic sensor minus the reading of the first magnet 112 is the reading of the external magnet in the environment.

In the embodiment, the acceleration sensor and the magnetic sensor are preferably three-dimensional sensors, and may also be one-dimensional sensors, but when they are one-dimensional sensors, the sensing direction of the magnetic sensor and the acceleration sensor should be along the long axis of the capsule endoscope 110.

In the embodiment, by measuring the tilt angle of the capsule endoscope and the ambient magnetic field of the capsule endoscope, an external magnetic force and direction required for the capsule endoscope to reach the quasi-suspended state can be further calculated, so that the capsule endoscope can be moved in the quasi-suspended state. In detail, a critical magnetic field value for suspension of the capsule endoscope is obtained according to the ambient magnetic field; a traction force on the capsule endoscope is adjusted according to the critical magnetic field value for suspension; and the movement of the capsule endoscope is controlled in a horizontal and/or vertical direction in the quasi-suspended state.

The center of gravity of the capsule endoscope 110 is in the vicinity of the long axis of the capsule endoscope 110 at a distance deviation of less than 2 mm, preferably, at a distance deviation of less than 0.5 mm.

FIGS. 2 to 7 show various situations of a method for controlling the capsule endoscope according to embodiments of the present invention. In the embodiment, a dual-camera capsule endoscope is preferably used, or a single-camera capsule endoscope can also be used. But when the single-camera capsule endoscope is used and the capsule endoscope is at the lower wall of the target area, the capsule endoscope needs to be flipped 180° so that the camera is facing downward. In the following embodiment, the dual-camera capsule endoscope is taken as an example. Therefore, no matter whether the capsule endoscope is on the upper wall or the lower wall of the target area, it is not needed to change its orientation. As shown in FIGS. 2 to 7, the dual-camera capsule endoscope is described in terms of being on the upper wall of the stomach and the lower wall of the stomach.

In the embodiment, the direction of magnetization of the first magnet in the capsule endoscope 110 is along the long axis of the capsule endoscope, and the capsule endoscope 110 is oriented vertically upward when taking images. Preferably, the second magnet is magnetized in the same direction as the first magnet, but in this case, complete symmetry would cause the capsule endoscope 110 to spin during critical suspension and result in unclear images. So, the direction of magnetization of the second magnet is tilted to the ground by a small angle of 0 to 20°. That is, there is a small angle between the direction of magnetization of the second magnet and the vertical direction, and the angle is a magnitude of 0-20°. Preferably, the small angle is 5°. In the following embodiments, the second magnet is magnetized in the same direction as the first magnet means that the second magnet is tilted to the ground by the small angle.

Figure 2:
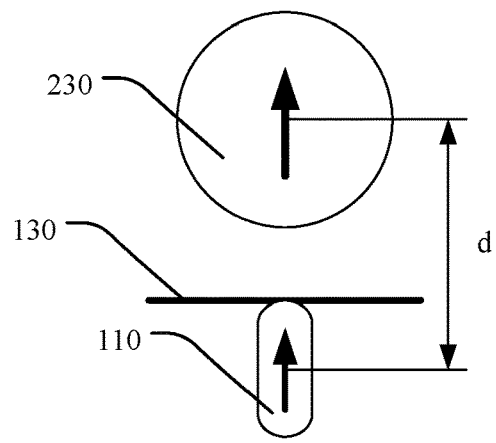
FIGS. 2 to 7 show various situations of a method for controlling the capsule endoscope according to embodiments of the present invention.
Figure 3:
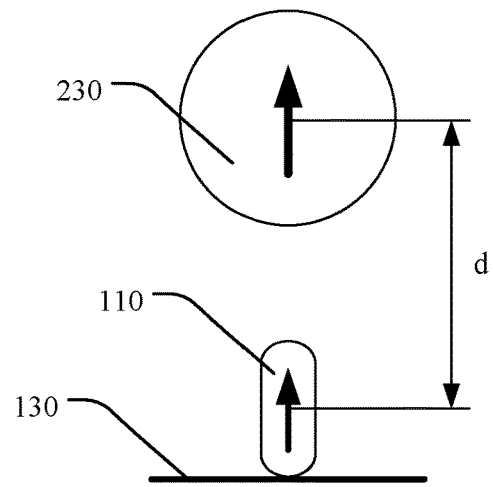

FIG. 2 and FIG. 3 illustrate the situations where the capsule endoscope is located on the upper wall of the stomach and the lower wall of the stomach when the stomach has air.

Referring to FIG. 2 and FIG. 3, the direction of magnetization of the capsule endoscope 110 (the direction shown by the arrows in FIG. 2 and FIG. 3) is consistent with the direction of magnetization of the external second magnet 230. The second magnet is located directly above the capsule endoscope 110. The capsule endoscope 110 is located below the upper wall 130 of the stomach (or above the lower wall 130 of the stomach), at a distance d from the second magnet 230. The distance d is the distance from the center of the capsule endoscope 110 to the center of the second magnet 230.

At this point, the forces on the capsule endoscope 110 include a traction force $F_{magnetic}$ from the second magnet 230 and the gravitational force $W_{capsule}$ of the capsule endoscope 110 itself. The traction force $F_{magnetic}$ is upward. When the capsule endoscope 110 is in the quasi-suspended state, the traction force $F_{magnetic}$ is equal to the gravitational force $W_{capsule}$, formula (4) can be obtained according to formulas (1) to (3) below.

$$F = \frac{\mu_0}{4\pi} \times \frac{6Mm}{d^4} = W \qquad (1)$$

$$d = \left(\frac{\mu_0}{4\pi} \times \frac{6Mm}{W}\right)^{1/4} \qquad (2)$$

Wherein, the magnetic sensor in the capsule endoscope 110 detects a critical magnetic field value for suspension $B_{cr}$. The critical magnetic field value for suspension $B_{cr}$ is calculated by the formula (4) below.

$$B_{cr} = \frac{\mu_0}{4\pi} \times \frac{2M}{d^3} \qquad (3)$$

$$B_{cr} = \frac{\mu_0 M}{2\pi} \times \left(\frac{\mu_0}{4\pi} \times \frac{6Mm}{W}\right)^{-3/4} \qquad (4)$$

In the above formulas (1) to (4), M is the magnetic moment of the second magnet 230, m is the magnetic moment of the first magnet in the capsule endoscope 110, $\mu_0$ is vacuum permeability, d is the distance from the center of the capsule endoscope 110 to the center of the second magnet 230, and W is the gravitational force of the capsule endoscope. F is the traction force from the second magnet 230, that is, the attraction force between the second magnet 230 (magnet outside the capsule endoscope) and the first magnet (magnet inside the capsule endoscope).

When the capsule endoscope 110 is located on the upper wall of the stomach, $B > B_{cr}$, e.g. $B_{set} = 1.05 B_{cr}$.

When the capsule endoscope 110 is located on the lower wall of the stomach, $B < B_{cr}$, e.g. $B_{set} = 0.95 B_{cr}$.

B and $B_{set}$ refer to magnetic field values of the second magnet 230, and $B_{set}$ is a corrected magnetic field value. The corrected magnetic field value is obtained according to the critical magnetic field value for suspension $B_{cr}$. At this point, the friction of the capsule endoscope has the following relationship: $f_{friction} = \mu N$. When $B \sim B_{cr}$, $f_{friction} \approx 0$. Therefore, by constantly adjusting the height of the second magnet according to the corrected magnetic field value $B_{set}$, the traction force of the capsule endoscope is adjusted, the capsule endoscope can reach the quasi-suspended state, and with the horizontal movement of the second magnet 230, the capsule endoscope can be translated in a near suspended state.

Figure 4:
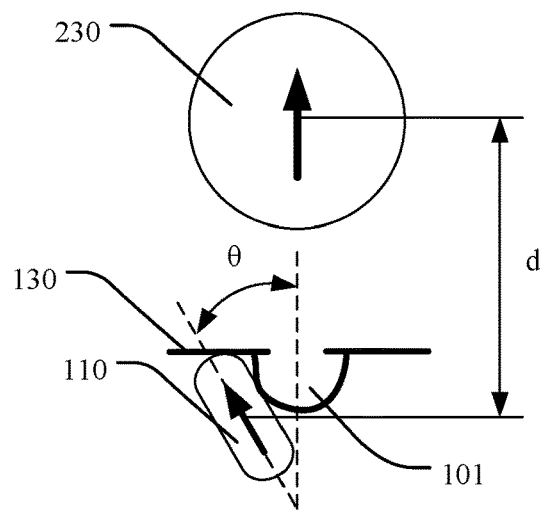
Figure 5:
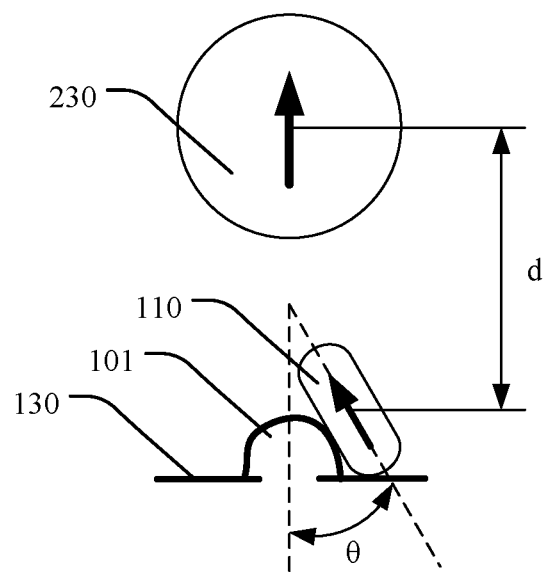

FIG. 4 and FIG. 5 illustrate the situations where the capsule endoscope is located on the upper wall of the stomach and the lower wall of the stomach when there is an obstacle in the stomach.

Referring to FIG. 4 and FIG. 5, since the stomach has an obstacle 101, the capsule endoscope 110 is tilted when it encounters the obstacle 101 while traveling along the stomach wall. At which time there is an angular difference, i.e., a tilt angle θ, between the direction of magnetization of the capsule endoscope 110 (the direction shown by the arrows in the FIG. 4 and FIG. 5) and direction of magnetization of the external second magnet 230. The second magnet is located directly above the capsule endoscope 110. The capsule endoscope 110 is located below the upper wall 130 of the stomach (or above the lower wall 130 of the stomach), at a distance d from the second magnet 230. The distance d is the distance from the center of the capsule endoscope 110 to the center of the second magnet 230.

At this point, the forces on the capsule endoscope 110 include the traction force $F_{magnetic}$ from the second magnet 230 and the gravitational force $W_{capsule}$ of the capsule endoscope 110 itself. The traction force $F_{magnetic}$ is upward. But since the capsule endoscope 110 is tilted when it encounters the obstacle, the tilt angle of the capsule endoscope 110 needs to be calculated by the acceleration sensor. That is, when the tilt angle of the capsule endoscope is greater than zero, it means that the capsule endoscope encounters an obstacle. Therefore, when the capsule endoscope 110 is in the quasi-suspended state, formula (8) can be obtained according to the formulas (5) to (7) below.

$$F = \frac{\mu_0}{4\pi} \times \frac{6Mm\cos\theta}{d^4} = W \quad (5)$$

$$d = \left(\frac{\mu_0}{4\pi} \times \frac{6Mm\cos\theta}{W}\right)^{1/4} \quad (6)$$

$$\cos\theta = \frac{g_z}{g} \quad (7)$$

Wherein, the magnetic sensor in the capsule endoscope 110 detects the critical magnetic field value for suspension $B_{cr}$. The critical magnetic field value for suspension $B_{cr}$ is calculated by the formula (8) below.

$$B_{cr}(\theta) = \frac{\mu_0 M}{2\pi} \times \left(\frac{\mu_0}{4\pi} \times \frac{6Mm\cos\theta}{W}\right)^{-3/4} \quad (8)$$

In the above formulas (5) to (8), M is the magnetic moment of the second magnet 230, m is the magnetic moment of the first magnet in the capsule endoscope 110, $\mu_0$ is the vacuum permeability, d is the distance from the center of the capsule endoscope 110 to the center of the second magnet 230, and W is the gravitational force of the capsule endoscope. F is the traction force from the second magnet 230, that is, the attraction force between the second magnet 230 (magnet outside the capsule endoscope) and the first magnet (magnet inside the capsule endoscope). $g_z$ is the axial acceleration component of the capsule endoscope, and g is the gravitational acceleration. In the embodiment of the present invention, the gravitational acceleration g is the total acceleration measured by the acceleration sensor, g=$\sqrt{g_x^2+g_y^2+g_z^2}$, of which the value is not significantly different from 9.8. In some alternative embodiments, it can be considered that the gravitational acceleration g is a known parameter (e.g., 9.8), so a gravity sensor may be used instead of an acceleration sensor to reduce costs and to reduce the amount of calculations.

When the capsule endoscope is located on the upper wall of the stomach, B>$B_{cr}(\theta)$, e.g. $B_{set}(\theta)$=1.05$B_{cr}(\theta)$.

When the capsule endoscope is located on the lower wall of the stomach, B<$B_{cr}(\theta)$, e.g. $B_{set}(\theta)$=0.95$B_{cr}(\theta)$.

B is the magnetic field value of the second magnet 230. When the capsule endoscope is vertically upward, i.e., θ=0°, cos θ=1, which is a suspended state of the capsule endoscope without obstacle, so the formula of $B_{cr}(\theta)$ includes the case of the capsule endoscope being vertically upward, and is used as a general formula for the cases with or without obstacles.

The friction of the capsule endoscope has the following relationship: $f_{friction}$=μN. When B~$B_{cr}$, $f_{friction}$≈0. Therefore, by constantly adjusting the height of the second magnet according to the corrected magnetic field value $B_{set}$, the capsule endoscope can be translated in a near suspended state.

In the embodiment, by changing the distance between the second magnet and the capsule endoscope 110, and thus changing the traction force on the capsule endoscope 110 along the long axis of the capsule endoscope 110, the capsule endoscope is moved along the long axis of the capsule endoscope 110, and achieves the quasi-suspended state. Furthermore, with the horizontal movement of the second magnet 230, the capsule endoscope can cross the obstacle. Since it is the changing of magnetic field gradient in the vertical direction of the second magnet that is used to cross the obstacle, it can be successful regardless of the size of the obstacle.

Figure 6:
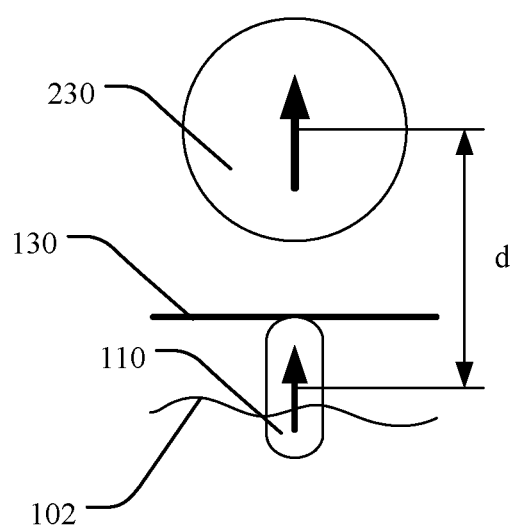
Figure 7:
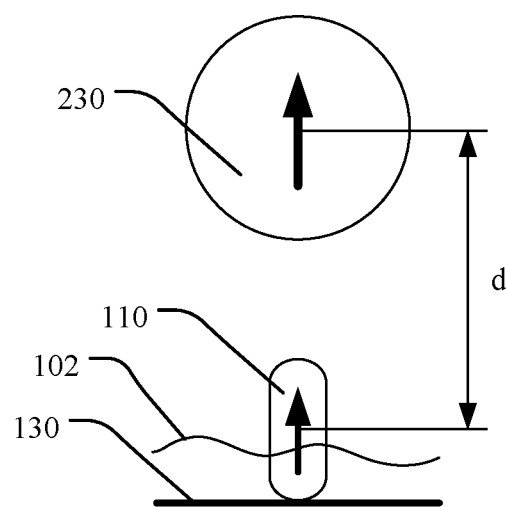

FIG. 6 and FIG. 7 illustrate the situations where the capsule endoscope 110 is located on the upper wall of the stomach and the lower wall of the stomach when there is liquid 102 in the stomach.

Referring to FIG. 6 and FIG. 7, the direction of magnetization of the capsule endoscope 110 (the direction shown by the arrows in FIG. 6 and FIG. 7) is consistent with the direction of magnetization of the external second magnet 230. The second magnet is located directly above the capsule endoscope 110. The capsule endoscope 110 is located below the upper wall 130 of the stomach (or above the lower wall 130 of the stomach), at a distance d from the second magnet 230. The distance d is the distance from the center of the capsule endoscope 110 to the center of the second magnet 230.

At this point, the forces on the capsule endoscope 110 include the traction force $F_{magnetic}$ from the second magnet 230, buoyancy force and the gravitational force $W_{capsule}$ of the capsule endoscope 110 itself. The traction force $F_{magnetic}$ is upward. So, when the capsule endoscope 110 is in the quasi-suspended state, formula (13) can be obtained according to formulas (9) to (12) below.

$$F_{magnetic} = W_{capsule} - \rho v \quad (9)$$

$$F = \frac{\mu_0}{4\pi} \times \frac{6Mm\cos\theta}{d^4} = W - \rho v \quad (10)$$

$$d = \left(\frac{\mu_0}{4\pi} \times \frac{6Mm\cos\theta}{W - \rho v}\right)^{1/4} \quad (11)$$

$$\cos\theta = \frac{g_z}{g} \quad (12)$$

Wherein, the magnetic sensor in the capsule endoscope 110 detects the critical magnetic field value for suspension $B_{cr}$. $B_{cr}$ relates to formula (13) below. The critical magnetic field value for suspension $B_{cr}$ is obtained based on the gravitational force, the tilt angle and buoyancy force of the capsule endoscope.

$$B_{cr}(\theta) = \frac{\mu_0 M}{2\pi} \times \left(\frac{\mu_0}{4\pi} \times \frac{6Mm\cos\theta}{W - \rho v}\right)^{-3/4} \quad (13)$$

In the above formulas (9) to (13), M is the magnetic moment of the second magnet 230, m is the magnetic moment of the first magnet in the capsule endoscope 110, $\mu_0$ is the vacuum permeability, d is the distance from the center of the capsule endoscope 110 to the center of the second magnet 230, W is the gravitational force of the capsule endoscope, F is the attraction force between the second magnet 230 (external magnet) and the first magnet (magnet inside the capsule), θ is the tilt angle of the capsule endoscope 110, $g_z$ is the axial acceleration component of the capsule endoscope, g is the gravitational acceleration, ρ is the specific gravity of the liquid in the stomach, and v is the volume of the capsule endoscope. In the embodiment of the present invention, the gravitational acceleration g is the total acceleration measured by the acceleration sensor, $g = \sqrt{g_x^2 + g_y^2 + g_z^2}$, of which the value is not significantly different from 9.8. In some alternative embodiments, it can be considered that the gravitational acceleration g is a known parameter (e.g., 9.8), so a gravity sensor may be used instead of the acceleration sensor to reduce costs and to reduce the amount of calculations.

When the capsule endoscope is located on the upper wall of the stomach, $B > B_{cr}(\theta)$, e.g. $B_{set}(\theta) = 1.05 B_{cr}(\theta)$.

When the capsule endoscope is located on the lower wall of the stomach, $B < B_{cr}(\theta)$, e.g. $B_{set}(\theta) = 0.95 B_{cr}(\theta)$.

The friction of the capsule endoscope has the following relationship: $f_{friction} = \mu N$. When $B \sim B_{cr}$, $f_{friction} \approx 0$. Therefore, by constantly adjusting the height of the second magnet according to the corrected magnetic field value $B_{set}$, the traction force of the capsule endoscope is adjusted, the capsule endoscope can reach the quasi-suspended state, and with the horizontal movement of the second magnet 230, the capsule endoscope can be translated in a near suspended state.

In the embodiment shown in FIG. 2 and FIG. 7, the critical magnetic field value for suspension $B_{cr}$ is calculated by the formulas, and in other embodiments, it can also be obtained from experimental test results. Specifically, the steps of obtaining the critical magnetic field value for suspension $B_{cr}$ comprise: placing the capsule endoscope directly below the second magnet, adjusting the height of the second magnet by a small distance, and recording the critical magnetic field value for suspension $B_{cr}$ when the capsule endoscope is about to be sucked up or to drop down by the second magnet; changing the environment in which the capsule endoscope is subjected, e.g. placing the capsule endoscope in the liquid directly below the second magnet, adjusting the height of the second magnet by a small distance, and recording the critical magnetic field value for suspension $B_{cr}$ when the capsule endoscope is about to be sucked up or to drop down by the second magnet; performing a plurality of experiments and recording the data to obtain accurate critical magnetic field value for suspension $B_{cr}$.

Figure 8:
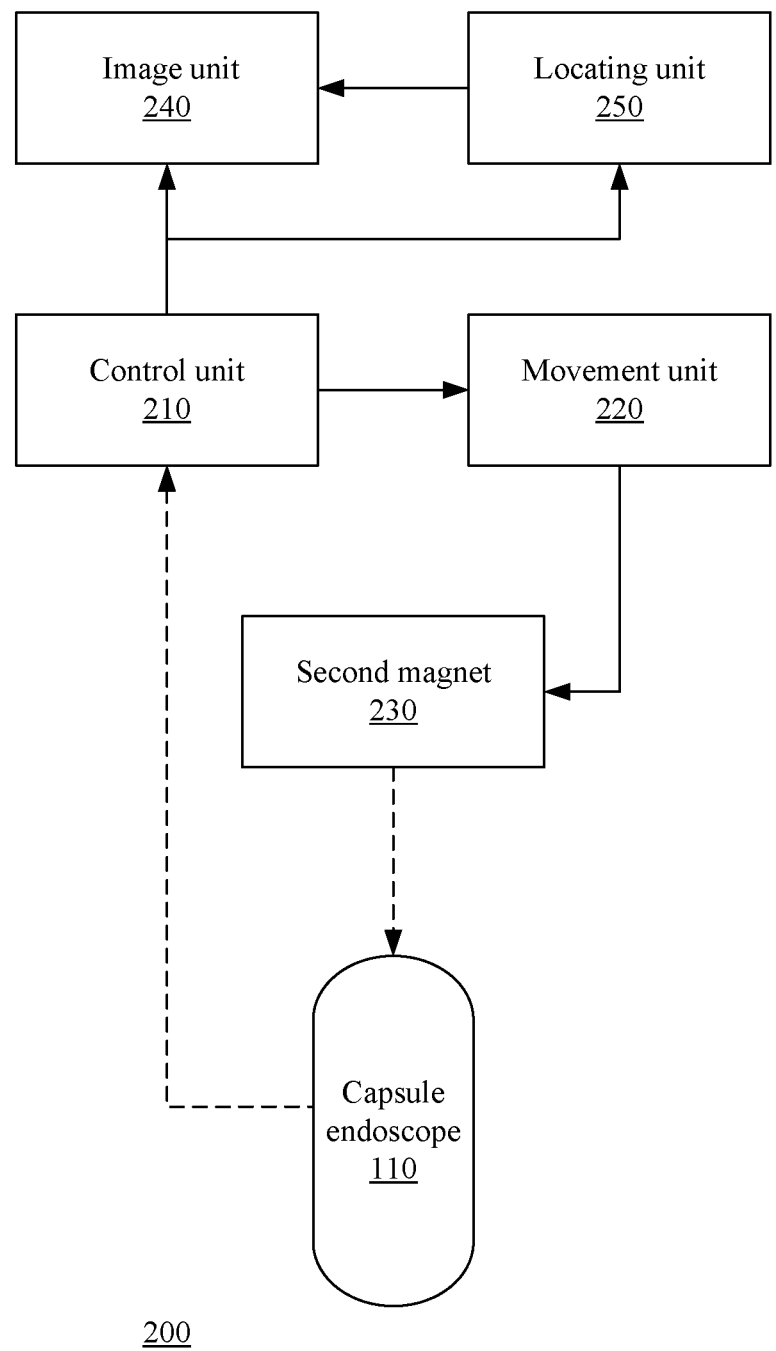
FIG. 8 is a schematic illustration of a system for controlling the capsule endoscope according to an embodiment of the present invention.

FIG. 8 is a schematic illustration of a system for controlling the capsule endoscope according to an embodiment of the present invention. Referring to FIG. 8, the system for controlling the capsule endoscope 200 comprises the capsule endoscope 110 and a control unit 210, a movement unit 220, a second magnet 230, an image unit 240, and a locating unit 250. The control unit 210, the movement unit 220, the second magnet 230, the image unit 240, and the locating unit 250 are outside the capsule endoscope 200.

The control unit 210 receives the magnetic field data measured by the magnetic sensor and the acceleration data measured by the acceleration sensor in the capsule endoscope 110 and calculates the traction force required to keep the capsule endoscope 110 in the quasi-suspended state based on the magnetic field data and acceleration data, and then generates a control signal. That is, the control unit 210 receives data transmitted from the capsule endoscope 110 to calculate a critical magnetic field value for suspension and to obtain the control signal based on the critical magnetic field value for suspension.

The movement unit 220 receives the control signal and controls the second magnet 230 to move in the horizontal and/or vertical direction according to the control signal, which in turn controls the movement of the capsule endoscope 110 located in the target area in the horizontal or vertical direction. The first magnet of the capsule endoscope 110 is controlled by moving the second magnet 230, and the capsule endoscope 110 is in the quasi-suspended state as moving in the horizontal and/or vertical direction. The movement unit 220 may specifically be a robot with three-dimensional movement, a right angle coordinate robot or a robotic arm.

The second magnet 230 may be a permanent magnet or an electromagnet. When the second magnet 230 is a permanent magnet, the traction force on the capsule endoscope 110 is controlled by changing the distance between the second magnet 230 and the first magnet in the vertical direction. When the second magnet 230 is an electromagnet, the traction force on the capsule endoscope 110 is controlled by controlling the distance between the second magnet and the first magnet in the vertical direction or the current of the second magnet 230, so as to keep the capsule endoscope 110 in the quasi-suspended state.

The image unit 240 is configured to receive a plurality of images captured by the capsule endoscope 110, and obtain a panoramic image of the target area based on the captured images. Since the capsule endoscope 110 moves along the wall of the target area under the control of the second magnet 230 and captures images in the target area, a panoramic image of the target area can be synthesized from the captured images. Meanwhile, a three-dimensional spatial structure of the target area can be built according to the panoramic image, which facilitates the examination of the target area and improves the accuracy.

The locating unit 250 is used to record position information and movement trajectory of the capsule endoscope 110. When the capsule endoscope 110 moves along the wall of the target area, the locating unit 250 can record the position information and movement trajectory of the capsule endoscope 110 in real time, or the locating unit 250 can record the position information of the capsule endoscope 110 once every certain time. While the image unit 240 can build the three-dimensional spatial structure of the target area based on the position information and/or the movement trajectory to facilitate the examination and improve the accuracy.

In the embodiment, the system for controlling the capsule endoscope 200 may use either manual control or automatic control to control the movement of the capsule endoscope 110 in the horizontal and/or vertical direction to collect images of the target area. The movement of the second magnet in the horizontal and/or vertical direction can also use a manual control means controlled by the movement unit and an automatic control means controlled by the control unit.

In the manual control means, the capsule endoscope 110 needs to be placed into the target area first. The specific steps comprises: first, placing the capsule endoscope to a first point of the target area through the movement unit; second, attracting the capsule endoscope to the upper wall of the target area, activating a quasi-suspension mode of the upper wall, and automatically adjusting the height of the second magnet; third, controlling the capsule endoscope to travel in the horizontal direction through the movement unit and taking images; fourth, switching to a quasi-suspension mode of the lower wall, and automatically adjusting the height of the external magnet; fifth, controlling the capsule endoscope to travel in the horizontal direction through the movement unit and taking images; sixth, changing orientation of the target area and repeating the above steps. The quasi-suspension mode of the upper wall means the capsule endoscope is in the quasi-suspension state on the upper wall. The quasi-suspension mode of the lower wall means the capsule endoscope is in the quasi-suspension state on the lower wall.

In the manual control method, the system 200 automatically adjusts the height of the second magnet continuously according to the critical magnetic field value for suspension $B_{cr}$ obtained from the test. That is, the height of the capsule endoscope in the Z direction (vertical direction) is automatically adjusted by the system 200 to achieve near-suspension translation, so the manipulator only needs to control the movement in the horizontal direction to obtain the image of the corresponding position in the target area.

In the embodiment, the manual control means can control the capsule endoscope 110 to move to a designated position for image collection, which improves the accuracy of scanning the target area.

In the automatic control means, the specific steps include: 1. placing the capsule endoscope to a first point of the target area; 2. attracting the capsule endoscope to the upper wall of the target area, activating a quasi-suspension mode of the upper wall, and automatically adjusting the height of the external magnet; 3. zigzag scanning the upper wall of the target area; 4. zigzag scanning the lower wall of the target area. The automatic control means is executed according to the command of the control unit.

Figure 9:
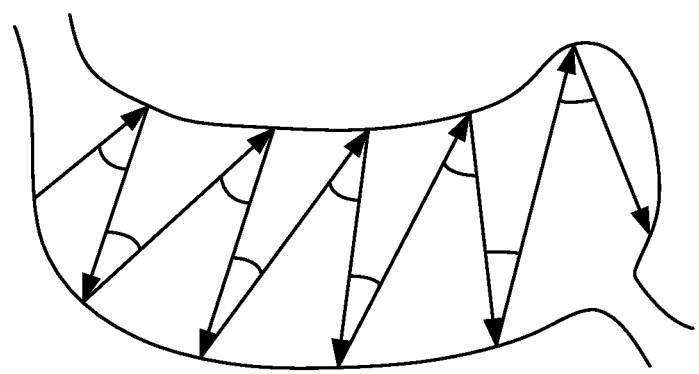
FIG. 9 shows a zigzag scanning of the capsule endoscope against stomach wall according to an embodiment of the present invention.
Figure 10:
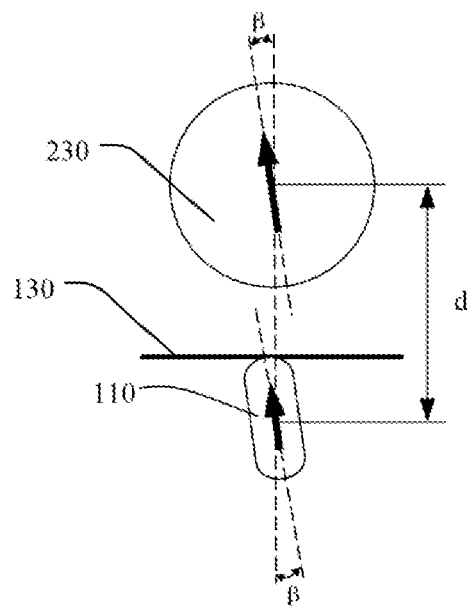
FIGS. 10 to 11 show same embodiments of FIGS. 2 and 4 to illustrate angle between the direction of magnetization of the second magnet and the vertical direction, angel β, of the present invention.
Figure 11:
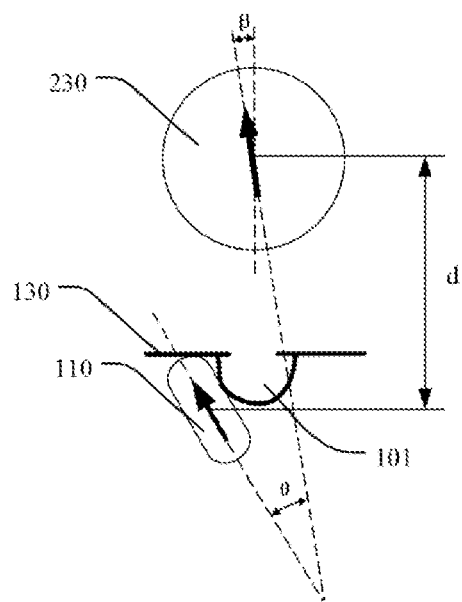

In the automatic control means, referring to FIG. 9, the specific steps of zigzag scanning comprise: 3.1, tilt an angle in a XY plane of the capsule endoscope to move linearly, and since the surface of the target area is arc-shaped, the second magnet controls the capsule endoscope to move in the Z direction according to the feedback thereof; 3.2, when the descending gradient in the Z direction during the linear motion of the capsule endoscope exceeds a threshold value, it is considered that the capsule endoscope reaches the edge of the target area, and it continues moving after a deflection of θ angle; if it is needed to make the scan route tight, reduce the θ angle, and if the scan route is too tight, increase the θ angle; 3.3, repeat 3.1-3.2 until the gradient in the Z direction on the XY line is greater than the threshold.

In the embodiment, the automatic control means improves the examination efficiency. Based on the images of the target area obtained by the automatic control means, the physician can generally determine the location of a lesion, and then perform a further examination of the lesion using the manual control means, which improves examination efficiency and accuracy.

In the automatic and/or manual means, a panoramic image and a three-dimensional spatial structure of the target area can be obtained by combining the images of the upper wall and the lower wall of the target area.

Since the capsule endoscope is in a quasi-suspended state, the friction with the target area is greatly reduced, and the injury to the target area while moving is also greatly reduced.

According to the aspects of the present invention, the capsule endoscope is controlled to be in the quasi-suspended state, that is, the mutual attraction between the second magnet and the first magnet is equal to or slightly greater than the weight of the capsule endoscope when it is at the upper wall of the target area, equal to or slightly less than the weight of the capsule endoscope when it is at the lower wall of the target area, and offsets the buoyancy force when there is liquid in the target area, so that the pressure between the capsule endoscope and the stomach wall tends to zero, friction is greatly reduced, and the scanning of the target area is more accurate.

According to the system and method for controlling the capsule endoscope provided by the present invention, when the capsule endoscope encounters an obstacle, the capsule endoscope is controlled to move in the vertical direction by a change in magnetic field gradient of the second magnet in the vertical direction, to bring the capsule endoscope to the quasi-suspended state, and the capsule endoscope is controlled to move in the horizontal direction by manipulating the second magnet to move in the horizontal direction to cross the obstacle.

In the present invention, two control methods, i.e. automatic scanning and manual scanning are provided. If the position of interest is visible from the image captured by the automatic scanning method, the capsule endoscope can be controlled by the manual scanning method to move to the designated position of the target area for scanning, which improves the efficiency and accuracy of examination.

The foregoing description of the embodiments of the invention has been presented for the purposes of illustration and description. It is not intended to be exhaustive or to limit the present invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the present invention.

What is claimed is:

1. A system for controlling a capsule endoscope, comprising:
   a capsule endoscope comprising an image acquisition module, a first magnet, a battery module, a wireless module, and a sensor module;
   a control unit for receiving data transmitted from the capsule endoscope to calculate a critical magnetic field value for suspension and obtaining a control signal based on the critical magnetic field value for suspension;
   a movement unit and a second magnet, the movement unit controlling the second magnet to move in a horizontal and/or vertical direction according to the control signal,
   wherein the movement of the first magnet is controlled by moving the second magnet, the capsule endoscope is in a quasi-suspended state while moving along the stomach wall in the horizontal and/or vertical direction, and the data transmitted by the capsule endoscope comprises a value of buoyancy force, a value of gravitational force, and a magnetic field value, wherein there is an angle between the direction of magnetization of the second magnet and the vertical direction, and the angle has a magnitude of 5 to 20°.

2. The system of claim 1, wherein the sensor module comprises a magnetic sensor and an acceleration sensor.

3. The system of claim 2, wherein the magnetic sensor is located not in close proximity from the first magnet and the acceleration sensor is a gravity sensor.

4. The system of claim 2, wherein the sensing directions of the magnetic sensor and the acceleration sensor are along the long axis of the capsule endoscope.

5. The system of claim 2, wherein the acceleration sensor is used to measure a tilt angle of the capsule endoscope, and the capsule endoscope encounters an obstacle when the tilt angle is not 0.

6. The system of claim 1, wherein the direction of magnetization of the first magnet is along the long axis of the capsule endoscope.

7. The system of claim 1, wherein the movement unit comprises a robot with three-dimensional movement, a right angle coordinate robot or a robotic arm.

8. The system of claim 1, wherein the second magnet comprises a permanent magnet or an electromagnet.

9. The system of claim 1, further comprising:
an image unit, which receives a plurality of images captured by the capsule endoscope and builds a three-dimensional spatial structure for the target area.

10. The system of claim 9, wherein the image unit obtains a panoramic image of the target area according to the captured images, and the image unit obtains the three-dimensional spatial structure of the target area according to the panoramic image.

11. The system of claim 9, further comprising:
a locating unit, which records position information and/or movement trajectory of the capsule endoscope; and the image unit obtains the three-dimensional spatial structure of the target area.

12. The system of claim 1, wherein the means for controlling the movement of the second magnet in the horizontal and/or vertical direction comprises manual control means controlled by the movement unit and automatic control means controlled by the control unit.

13. A capsule endoscope,
comprising a first magnet inside the capsule endoscope, and a second magnet outside the capsule endoscope controlling a movement of the capsule endoscope; the capsule endoscope configured to be use by a method, the method comprising:
measuring a magnetic field value of an environment in which the capsule endoscope is in;
obtaining a critical magnetic field value for suspension of the capsule endoscope according to the magnetic field value of the environment;
adjusting a traction force on the capsule endoscope according to the critical magnetic field value for suspension; and
controlling the movement of the capsule endoscope in a horizontal and/or vertical direction, wherein the movement of the first magnet is controlled by moving the second magnet, and the capsule endoscope is in a quasi-suspended state as moving along the stomach wall in the horizontal and/or vertical direction, wherein there is an angle between the direction of magnetization of the second magnet and the vertical direction, and the angle has a magnitude of 5 to 20°.

14. The capsule endoscope of claim 13, wherein the magnetic field value is measured by a magnetic sensor, and a tilt angle is measured by an acceleration sensor.

15. The capsule endoscope of claim 13, wherein the critical magnetic field value for suspension is obtained based on the gravitational force of the capsule endoscope, tilt angle of the capsule endoscope and buoyancy force of the capsule endoscope.

16. The capsule endoscope of claim 15, wherein when the tilt angle of the capsule endoscope is greater than zero, it is determined that the capsule endoscope encounters an obstacle.

17. The capsule endoscope of claim 16, wherein when the capsule endoscope encounters an obstacle, the capsule endoscope is controlled to move in the vertical direction by a change in magnetic field gradient of the second magnet in the vertical direction, and the capsule endoscope is controlled to move in the horizontal direction by manipulating the second magnet to move in the horizontal direction to cross the obstacle.

18. The capsule endoscope of claim 13, wherein adjusting the traction force on the capsule endoscope according to the critical magnetic field value for suspension further comprises:
obtaining a corrected magnetic field value according to the critical magnetic field value for suspension; and
adjusting the height of the second magnet according to the corrected magnetic field value, thereby adjusting the traction force on the capsule endoscope.

19. The capsule endoscope of claim 13, wherein the means for controlling the movement of the capsule endoscope in the horizontal and/or vertical direction comprises manual control means and automatic control means.

* * * * *